(12) United States Patent
Ueda

(10) Patent No.: US 11,386,765 B2
(45) Date of Patent: Jul. 12, 2022

(54) SERVER, MONITORING SYSTEM, TERMINAL, MONITORING DEVICE AND METHOD FOR MONITORING OF OXYGEN CONCENTRATOR

(71) Applicant: TEIJIN PHARMA LIMITED, Tokyo (JP)

(72) Inventor: Taishi Ueda, Tokyo (JP)

(73) Assignee: Teijin Pharma Limited, Tokyo (JP)

( * ) Notice: Subject to any disclaimer, the term of this patent is extended or adjusted under 35 U.S.C. 154(b) by 69 days.

(21) Appl. No.: 16/959,608

(22) PCT Filed: Feb. 13, 2019

(86) PCT No.: PCT/JP2019/005135
§ 371 (c)(1),
(2) Date: Jul. 1, 2020

(87) PCT Pub. No.: WO2019/163609
PCT Pub. Date: Aug. 29, 2019

(65) Prior Publication Data
US 2020/0388131 A1 Dec. 10, 2020

(30) Foreign Application Priority Data
Feb. 21, 2018 (JP) .............................. JP2018-028861

(51) Int. Cl.
*G08B 21/02* (2006.01)
*A61M 16/06* (2006.01)
(Continued)

(52) U.S. Cl.
CPC ......... *G08B 21/02* (2013.01); *A61M 16/0051* (2013.01); *A61M 16/0672* (2014.02);
(Continued)

(58) Field of Classification Search
CPC .... A61M 2202/0208; A61M 2230/435; A61M 16/101; A61M 2202/0007;
(Continued)

(56) References Cited

U.S. PATENT DOCUMENTS

2003/0208465 A1* 11/2003 Yurko .................... G06Q 10/10
2005/0188083 A1 8/2005 Biondi et al.
(Continued)

FOREIGN PATENT DOCUMENTS

CN 102740917 A 10/2012
CN 104399164 A 3/2015
(Continued)

OTHER PUBLICATIONS

International Search Report of PCT/JP2019/005135 dated Mar. 19, 2019 [PCT/ISA/210].
(Continued)

*Primary Examiner* — Daniel Previl
(74) *Attorney, Agent, or Firm* — Sughrue Mion, PLLC

(57) ABSTRACT

A server 20 for monitoring of the state of use of an oxygen concentrator 10 that concentrates oxygen in air and supplies it to a user, comprises a communication unit 25, and a processing unit 21 that uses the communication unit 25 to receive operation data indicating the state of operation of the oxygen concentrator 10 and usage data for the state of use by the user using the oxygen concentrator 10, measured by a measuring apparatus 11, 12, while also generating message information when either or both the usage data and operation data fail to satisfy the monitoring conditions, and sending the message information together with the usage data and operation data, using the communication unit 25.

14 Claims, 10 Drawing Sheets

(51) Int. Cl.
*A61M 16/10* (2006.01)
*G16H 40/67* (2018.01)
*A61M 16/00* (2006.01)

(52) U.S. Cl.
CPC .......... *A61M 16/101* (2014.02); *G16H 40/67* (2018.01); *A61M 2205/35* (2013.01); *A61M 2205/50* (2013.01); *A61M 2205/583* (2013.01); *A61M 2230/06* (2013.01); *A61M 2230/205* (2013.01); *A61M 2230/42* (2013.01)

(58) Field of Classification Search
CPC ........ A61M 2230/005; A61M 16/0672; A61M 2205/18; A61M 2205/3592; A61M 2205/583; A61M 2209/088; A61M 2205/3553; A61M 2205/502; A61M 16/0051; A61M 16/024; A61M 2230/205; A61M 2230/42; A61M 2016/0018; A61M 2205/332; A61M 2205/35; A61M 2205/50; A61M 2205/6009; A61M 2230/06; A61M 16/10; A61M 2205/3584; A61M 2016/1025; A61M 2205/3569; A61M 2205/581; A61M 2205/707; A61M 2205/7563; A61M 2205/8206; A61M 16/0003; A61M 16/0072; A61M 16/06; A61M 16/0677; A61M 16/0683; A61M 16/202; A61M 2016/0033; A61M 2205/582; A61M 2205/80; A61M 2205/8293; A61M 2230/50; A61M 2230/30; A61M 2230/63; A61M 16/1005; A61M 2016/003; A61M 2205/3303; A61M 2205/3507; A61M 2205/3561; A61M 2205/42; A61M 2209/01; A61M 2210/1025; A61M 2230/202; A61M 2230/40; A61M 2230/65; A61M 5/16886; G16H 20/40; G16H 40/67; G16H 40/63; G16H 50/20; G16H 10/60; G16H 15/00; G16H 30/20; G16H 40/20; G16H 40/60; G16H 50/30; G16H 30/40; G16H 50/70; G16H 70/20; G16H 40/40; G16H 20/13; G16H 20/17; G16H 80/00; A61B 5/0816; A61B 5/08; A61B 5/1455; A61B 2034/2065; A61B 2034/256; A61B 2560/0487; A61B 34/20; A61B 34/25; A61B 90/37; A61B 5/087; A61B 5/0022; A61B 5/01; A61B 5/746; A61B 10/007; A61B 2010/0087; A61B 2505/07; A61B 5/0002; A61B 5/0004; A61B 5/002; A61B 5/0024; A61B 5/021; A61B 5/02152; A61B 5/024; A61B 5/145; A61B 5/14542; A61B 5/201; A61B 5/208; A61B 5/4839; A61B 5/6819; A61B 5/747; A61B 8/04; A61B 8/12; A61B 90/90; G06N 20/00; G06N 20/10; G06N 20/20; G06N 3/0445; G06N 3/0454; G06N 5/003; G06N 5/02; G06N 5/04; G06N 7/005
USPC .......... 340/573.1, 426.1, 426.2, 426.21, 438, 340/463–464, 488, 525, 534, 539.22, 340/568.1, 588

See application file for complete search history.

(56) References Cited

U.S. PATENT DOCUMENTS

| | | | |
|---|---|---|---|
| 2006/0154642 A1* | 7/2006 | Scannell, Jr. .......... | G08B 7/066 455/404.1 |
| 2006/0213519 A1 | 9/2006 | Schmidt et al. | |
| 2007/0023039 A1 | 2/2007 | Ishizaki et al. | |
| 2009/0126736 A1* | 5/2009 | Taylor .................... | A61M 16/10 128/204.23 |
| 2011/0073107 A1 | 3/2011 | Rodman et al. | |
| 2011/0154241 A1* | 6/2011 | Skidmore ............. | G06F 3/0484 715/771 |
| 2013/0008438 A1* | 1/2013 | Sugawara ........... | A61M 16/101 128/202.24 |
| 2013/0275139 A1* | 10/2013 | Coleman ........... | A61M 16/0003 704/275 |
| 2014/0150796 A1 | 6/2014 | Milne | |
| 2014/0281650 A1* | 9/2014 | Gilbert ................ | H04L 12/2825 713/340 |
| 2015/0231551 A1 | 8/2015 | Wilkinson et al. | |
| 2019/0188415 A1* | 6/2019 | Sellberg ................ | G16H 10/60 |

FOREIGN PATENT DOCUMENTS

| | | |
|---|---|---|
| CN | 104969227 A | 10/2015 |
| CN | 105311721 A | 2/2016 |
| JP | 11-314903 A | 11/1999 |
| JP | 2004-287494 A | 10/2004 |
| JP | 2012-228415 A | 11/2012 |
| JP | 2017-084211 A | 5/2017 |
| JP | 2017-124096 A | 7/2017 |
| WO | 2005/016426 A1 | 2/2005 |
| WO | 2011/075601 A1 | 6/2011 |
| WO | 2014/100687 A2 | 6/2014 |

OTHER PUBLICATIONS

Written Opinion for PCT/JP2019/005135 dated Mar. 19, 2019 [PCT/ISA/237].

* cited by examiner

FIG. 7

| | Item | Units | Overall | Daytime — Resting period | Daytime — Exertion period | Nighttime — Sleeping period | Definition |
|---|---|---|---|---|---|---|---|
| | Inhalation time | Daily average | 20 hrs ▼ | | | | Inhalation time less than __ hours as the daily use average? |
| | Non-prescription flow rate operating time | Daily average | 30 min ▼ | | | | Operation at non-prescription flow rate more than __ minutes as the daily use average? |
| | Operation time | Daily average | 2 hrs ▼ | | | | Operation time less than __ hours as the daily use average? |
| | Cannula dislocation time | Daily average | ▼ | 30 min ▼ | 30 min ▼ | 1 hr ▼ | Cannula dislocation time more than __ minutes as the daily use average? |
| | Cannula bend alarm count | Cumulative for period | ▼ | | | | Cannula bend alarm has sounded a total of at least one time during the set period? |
| | SpO₂ (median/ average value) | % | 85% ▼ | 85% ▼ | 85% ▼ | 85% ▼ | SpO$_2$ (median/average value) below __ % during the set period? |
| | Pulse rate (median/ average value) | bpm | 80bpm ▼ | 80bpm ▼ | 80bpm ▼ | 80bpm ▼ | Pulse rate (median/average value) below __ bpm during the set period? |
| ☑ | | | | | | | |
| ☑ | | | | | | | |
| ☐ | | | | | | | |
| ☑ | | | | | | | |
| ☐ | | | | | | | |
| ☑ | | | | | | | |
| ☑ | | | | | | | |

| | Patient ID<br>Date of birth | Patient name | Gender | Usage data for last 30 days | | | | | | Next scheduled outpatient date |
|---|---|---|---|---|---|---|---|---|---|---|
| | | | | Number of days of use | Operation time (daily average) | Cannula dislocation time (daily average) | Cannula bend alarm count (cumulative for period) | Non-prescription flow rate operating time (daily average) | SpO₂ median (%) | |
| ☑ | A00003<br>July 23, 1960 | Oishi Jiro | Male | 28 days | 20 hrs, 30 min | 2 hrs, 05 min | 8 times | 9 hrs, 50 min | 94.3% | 2017/4/30 08:00 |
| ☐ | A00005<br>June 6, 1974 | Kato Ichiro | Male | 10 days | 18 hrs, 45 min | 1 hrs, 15 min | 1 time | 0 hrs, 00 min | 92.1% | |
| ☐ | A00002<br>January 4, 1980 | Kato Hanako | Female | 17 days | 19 hrs, 40 min | 0 hrs, 05 min | 15 times | 1 hrs, 40 min | 84.2% | |
| ☐ | A00013<br>January 4, 1980 | Kobayashi Sabuko | Female | 30 days | 15 hrs, 20 min | 8 hrs, 35 min | 4 times | 3 hrs, 45 min | 96.3% | 2017/5/10 10:00 |
| ☐ | A00023<br>June18, 1984 | Kobayashi Rokuro | Male | 20 days | 8 hrs, 05 min | 1 hrs, 09 min | 9 times | 0 hrs, 55 min | 91.6% | |
| ☐ | A00053<br>February 24, 1990 | Sato sachiko | Female | 26 days | 16 hrs, 25 min | 3 hrs, 55 min | 4 times | 2 hrs, 55 min | 90.2% | |

■ Message

901
- Short inhalation time.
- Long operation time at non-prescription flow rate.
- Short operation time.
- Long cannula dislocation time.
- Cannula bend alarm is sounding.

■ Usage state overview    902

| Item | March 1 to March 30 (902a) | January 30 to February 28 (902b) | December 31 to January 29 (902d) |
|---|---|---|---|
| Number of days of use | 25 days/30 days | 24 days/30 days | 20 days/30 days |
| Inhalation time (daily average) | 9 hrs, 54 min | 18 hrs, 42 min | 19 hrs, 48 min |
| Flow switching frequency (daily average) | 3.2 times | 3.0 times | 2.9 times |
| Non-prescription flow rate operating time (daily average) | 1 hrs, 54 min | 2 hrs, 14 min | 1 hrs, 45 min |

■ Usage state details    903

| Item | Overall (903a) | Daytime (by flow rate) | | | Night (by flow rate) | |
|---|---|---|---|---|---|---|
| | | Resting period (903c) | Exertion period (903d) | Other (903e) | Sleeping period (903f) | Other (903g) |
| Operation time (daily average) | 11 hrs, 24 min | 2 hrs, 48 min | 0 hrs, 24 min | 1 hrs, 48 min | 7 hrs, 6 min | 0 hrs, 18 min |
| Cannula dislocation time (daily average) | 2 hrs, 30 min | 0 hrs, 18 min | 0 hrs, 12 min | 0 hrs, 6 min | 1 hrs, 54 min | — |
| Cannula bend alarm count (cumulative for period) | 4 times | 1 time | — | — | 3 times | — |

■ SpO₂ · pulse rate    904

| Item | Overall (904a) | Daytime (by flow rate) | | | Night (by flow rate) | |
|---|---|---|---|---|---|---|
| | | Resting period (904c) | Exertion period (904d) | Other (904e) | Sleeping period (904f) | Other (904g) |
| SpO₂ (median) | 92.1% | 93.3% | 90.2% | 92.1% | 91.2% | 92.4% |
| Pulse rate (median) | 78bmp | 78bmp | 78bmp | 78bmp | 67bmp | 78bmp |

*Daily average: daily use average, with sleeping period as: 10 pm to 6 am

SERVER, MONITORING SYSTEM, TERMINAL, MONITORING DEVICE AND METHOD FOR MONITORING OF OXYGEN CONCENTRATOR

CROSS REFERENCE TO RELATED APPLICATIONS

This application is a National Stage of International Application No. PCT/JP2019/005135 filed Feb. 13, 2019, claiming priority based on Japanese Patent Application No. 2018-028861 filed Feb. 21, 2018.

FIELD

The present invention relates to a server, a monitoring system, a terminal, a monitoring device and a method for monitoring of an oxygen concentrator.

BACKGROUND

Conventionally, respiration gas supply devices (hereunder also referred to as "oxygen concentrators") have been developed for separating and concentrating oxygen in air for a patient with respiratory disease to obtain oxygen-enriched gas, and oxygen therapy using them has also become common.

Such oxygen therapy is often carried out while the patient is admitted to a medical institution, but when the patient's respiratory disease exhibits chronic symptoms making it necessary to carry out the oxygen therapy over long periods of time to mitigate and stabilize the symptoms, a treatment method is sometimes carried out in which the oxygen concentrator is set in the patient's home, and a tube called a cannula is used to deliver oxygen-enriched gas supplied by the oxygen concentrator near the nasal cavity of the patient to be inhaled by the patient. This type of treatment method is known as Home Oxygen Therapy, or "HOT".

Home Oxygen Therapy can be carried out by the steps of: (1) examination of the patient by a physician, (2) issuing of Home Oxygen Therapy instructions by the physician, while also indicate the prescription for the patient based on the examination, (3) setting of an oxygen concentrator in the home of the patient, as indicated in the instructions, (4) continuous inhalation of oxygen-enriched gas using the oxygen concentrator, and (5) periodic examination, such as once a month, by hospital visitation.

When Home Oxygen Therapy is begun, the physician issues the instructions which contain the prescription for the oxygen therapy to be undergone by the patient. The prescription indicates (1) the oxygen concentration of oxygen-enriched gas to be supplied to the patient, and (2) the flow rate and usage time for the oxygen-enriched gas to be supplied to the patient. Since inhalation of the oxygen-enriched gas is done at the patient's home, the physician cannot directly confirm that inhalation is performed with the indicated gas supply conditions, at the location where the inhalation is being performed. For example, the prescription specifies the oxygen flow rate when the patient is at rest during the day or is under exertion while moving, as well as during nighttime sleeping periods.

Periodically, such as once a month, the physician must directly meet with the patient during outpatient visitation to confirm whether or not inhalation is being carried out as prescribed, but responses by the patient to the physician's inquiry may in fact differ from the actual state of inhalation.

Since confirmation of the therapeutic effect of the Home Oxygen Therapy or planning of treatment policy are based on the results of meeting, examining, and questioning the patient by the physician on an outpatient basis, this opens up a risk if the response of the patient to physician inquiry differs from actuality.

PTL 1, for example, therefore proposes an oxygen concentrator that holds a recorded history of the supply conditions for oxygen-enriched gas supplied to a patient in Home Oxygen Therapy where oxygen-enriched gas is continuously inhaled at home, as supply history data, thus allowing the supply history data to be confirmed at a medical institution.

CITATION LIST

Patent Literature

[PTL 1] International Patent Publication No. WO2005/016426

SUMMARY

Technical Problem

Because of the many different types of supply history data for supply conditions of oxygen-enriched gas, it is a time-consuming and non-simple procedure for the physician to confirm all of the supply history data at the medical institution.

From the viewpoint of the physician, it is preferable to not have all of the supply history data of the patient constantly monitored, but rather to have a notification raised only when a certain monitoring parameter does not satisfy the monitoring conditions, so that the physician can study how to respond for the patient who has received the notification.

Therefore, it may be effective to monitor usage data indicating the state of use by the patient using the oxygen concentrator, and operation data indicating the state of operation of the oxygen concentrator, and to let the monitoring person know when the predetermined monitoring conditions are not satisfied.

The object of the present specification is provision of a server, monitoring system, terminal, monitoring device and method for monitoring usage data that indicate the state of use by a patient using an oxygen concentrator and operation data indicating the state of operation of the oxygen concentrator.

Solution to Problem

The server disclosed herein is a server for monitoring of the state of use of an oxygen concentrator that concentrates oxygen in air and supplies it to a user, the server having a communication unit, and a processing unit that uses the communication unit to receive operation data indicating the state of operation of the oxygen concentrator and usage data for the state of use by the user using the oxygen concentrator, measured by a measuring apparatus, while also generating message information when either or both the usage data and operation data fail to satisfy the monitoring conditions, and sending the message information together with the usage data and operation data, using the communication unit.

The monitoring system disclosed herein is a monitoring system for monitoring of the state of use of an oxygen concentrator that concentrates oxygen in air and supplies it to a user, the monitoring system having an oxygen concentrator that sends operation data indicating the state of operation, a measuring apparatus that measures and sends usage data indicating the state of use by the user using the oxygen concentrator, a server that receives the usage data and operation data, and when either or both the usage data and operation data fail to satisfy the monitoring conditions, generates message information and sends the message information together with the usage data and operation data, and a terminal that has a display and receives the message information together with the usage data and operation data, displaying them on the display.

The terminal disclosed herein is a terminal for monitoring of the state of use of an oxygen concentrator that concentrates oxygen in air and supplies it to a user, the terminal having a communication unit, a display, and a processing unit that uses the communication unit to receive from a server, message information generated by the server that has received operation data indicating the state of operation of the oxygen concentrator and usage data for the state of use by the user using the oxygen concentrator, measured by the measuring apparatus, when either or both the usage data and operation data fail to satisfy the monitoring conditions, and also the usage data and operation data, and displays the message information together with the usage data and operation data on the display.

The monitoring device disclosed herein is a monitoring device for monitoring of the state of use of an oxygen concentrator that concentrates oxygen in air and supplies it to a user, the monitoring device having an input unit, an output unit, and a processing unit which carries out to input operation data indicating the state of operation of the oxygen concentrator and usage data for the state of use by the user using the oxygen concentrator using the input unit, and when either or both the usage data and operation data fail to satisfy the monitoring conditions, carries out to generate message information and output the message information together with the usage data and operation data using the output unit.

The method disclosed herein is a monitoring method for monitoring of the state of use of an oxygen concentrator that concentrates oxygen in air and supplies it to a user, wherein the method includes obtaining input operation data indicating the state of operation of the oxygen concentrator and usage data for the state of use by the user using the oxygen concentrator, generating message information when either or both the usage data and operation data fail to satisfy the monitoring conditions, and displaying the message information together with the usage data and operation data on a display.

ADVANTAGEOUS EFFECTS OF INVENTION

The server disclosed herein can monitor usage data indicating the state of use by a patient using the oxygen concentrator and operation data indicating the state of operation of the oxygen concentrator, and can notify a monitoring person by generation of a message, when predetermined monitoring conditions fail to be satisfied.

The monitoring system disclosed herein can also monitor usage data indicating the state of use by a patient using the oxygen concentrator and operation data indicating the state of operation of the oxygen concentrator, and can notify a monitoring person by generation of a message, when predetermined monitoring conditions fail to be satisfied.

The terminal disclosed herein can likewise monitor usage data indicating the state of use by a patient using the oxygen concentrator and operation data indicating the state of operation of the oxygen concentrator, and can notify a monitoring person by generation of a message, when predetermined monitoring conditions fail to be satisfied.

The monitoring device disclosed herein can also monitor usage data indicating the state of use by a patient using the oxygen concentrator and operation data indicating the state of operation of the oxygen concentrator, and can notify a monitoring person by generation of a message, when predetermined monitoring conditions fail to be satisfied.

The method disclosed herein can likewise monitor usage data indicating the state of use by a patient using the oxygen concentrator and operation data indicating the state of operation of the oxygen concentrator, and can notify a monitoring person by generation of a message, when predetermined monitoring conditions fail to be satisfied.

BRIEF DESCRIPTION OF DRAWINGS

FIG. 7 is a diagram showing a display screen for setting of direction guide thresholds.

FIG. 8 is a diagram showing a display screen that displays the overall situation for the state of operation and state of use for a patient.

FIG. 9 is a diagram showing a display screen that displays the detailed situation for the state of operation and state of use for a patient.

DESCRIPTION OF EMBODIMENTS

A referred embodiment of the monitoring system disclosed herein will now be described with reference to the accompanying drawings. However, the technical scope of the invention is not limited to this embodiment, and includes the invention and its equivalents as laid out in the Claims.

Figure 1:
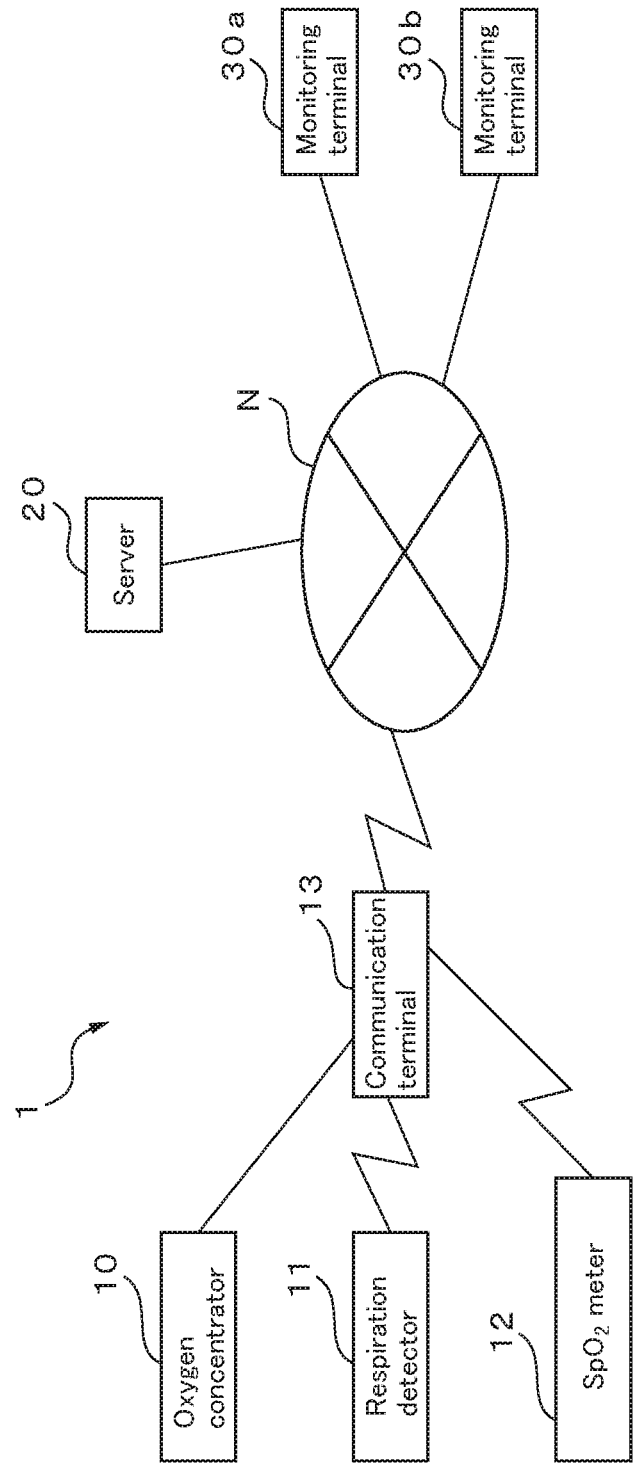
FIG. 1 is a diagram showing an embodiment of the monitoring system disclosed herein.
Figure 2:
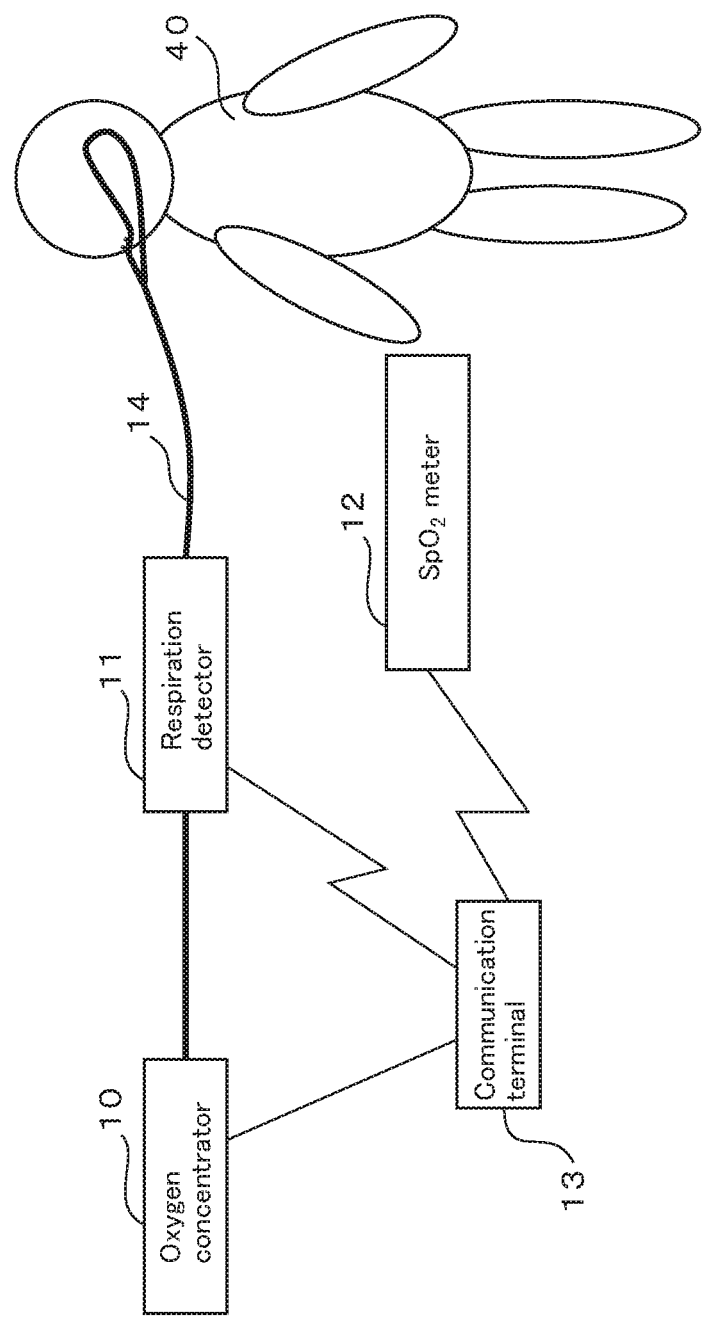
FIG. 2 is a diagram showing a patient using an oxygen concentrator and a measuring apparatus.
Figure 3:
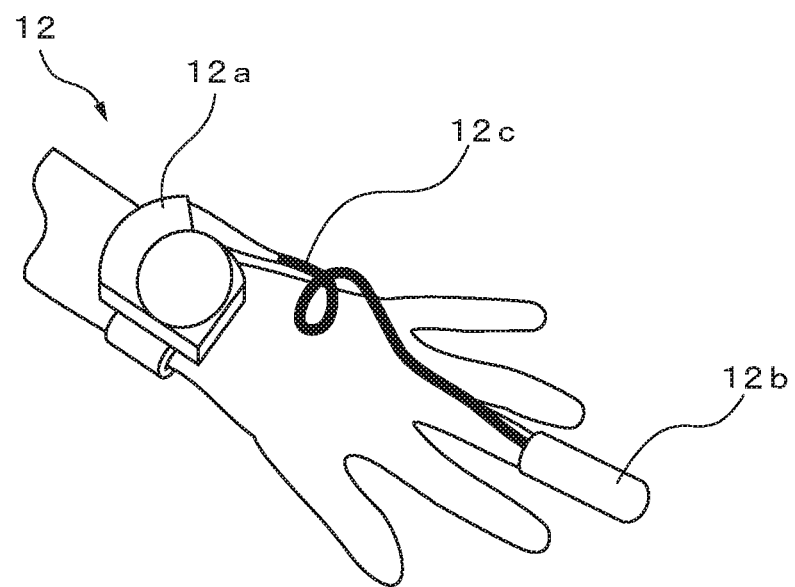
FIG. 3 is a diagram showing a state where an $SpO_2$ measuring apparatus is fitted onto the finger of a patient.

FIG. 1 is a diagram showing an embodiment of the monitoring system disclosed herein. FIG. 2 is a diagram showing a patient using an oxygen concentrator and a measuring apparatus. FIG. 3 is a diagram showing a state where an $SpO_2$ measuring apparatus is fitted onto the finger of a patient.

The monitoring system 1 of this embodiment comprises an oxygen concentrator 10, a respiration detector 11, a percutaneous arterial blood oxygen saturation meter ($SpO_2$ meter) 12, a communication terminal 13, a server 20 and monitoring terminals 30a, 30b.

As shown in FIG. 2, a patient 40 uses the oxygen concentrator 10 to carry out Home Oxygen Therapy, by continuous inhalation of oxygen-enriched gas at home.

The oxygen concentrator 10 is an apparatus that separates nitrogen in the air to supply high-concentration oxygen (oxygen-enriched gas), for use mainly in Home Oxygen Therapy. The oxygen concentrator 10 may be a pressure fluctuation adsorption-type oxygen concentrator which has an adsorption tube (not shown) packed with molecular sieve zeolite or lithium-based zeolite, as an adsorbent capable of selectively adsorbing nitrogen over oxygen, and supplies the pressurized air created by an air compressor (not shown) to extract the oxygen.

The oxygen produced by the oxygen concentrator 10 is supplied to the patient 40 using a cannula 14. The flow rate of the oxygen supplied by the oxygen concentrator 10 can be controlled using an operating unit (not shown). The flow rate of oxygen supplied by the oxygen concentrator 10 can usually be set based on a physician's prescription.

The oxygen concentrator 10 uses a communication terminal 13 to send operation data indicating the state of operation of the apparatus, through a network N to the server 20. The oxygen concentrator 10 communicates with the communication terminal 13 through a communication line, for example.

The communication terminal 13 sends the operation data received from the oxygen concentrator 10 to the server 20, through the network N by wired or wireless communication.

The state of operation of the oxygen concentrator 10 may include, for example, the set value for the oxygen flow rate, and a cannula bend alarm notification. The set value for the oxygen flow rate is the oxygen flow rate that has been set for the oxygen concentrator 10. A cannula bend alarm notification is a notification indicating a state in which the patient 40 cannot be supplied with sufficient generated oxygen through the cannula due to bending of the cannula. The oxygen concentrator 10 may also detect the respiration rate of the patient 40 as a state of operation.

A respiration detector 11 is provided within the cannula 14. The respiration detector 11 detects movement of gas through the cannula 14 and measures the state of use of the patient 40 who is using the oxygen concentrator, such as the respiration rate of the patient 40.

The respiration detector 11 sends the measured usage data to the server 20 through the network N, using the communication terminal 13. The respiration detector 11 communicates with the communication terminal 13 via short-range wireless communication, for example.

The communication terminal 13 sends the usage data received from the respiration detector 11 to the server 20, through the network N by either wired or wireless communication.

The usage data measured by the respiration detector 11 may be, for example, a respiration detection notification, notifying that respiration of the user has been detected, a cannula dislocation notification, notifying that the cannula has been dislocated, and the respiration rate. A respiration detection notification means detection of a state in which oxygen is being supplied to the patient 40 through the cannula 14 and respiration by the patient 40 has been detected. A cannula dislocation notification means detection of a state in which oxygen is being supplied to the patient 40 through the cannula 14, but respiration by the patient 40 is not detected. The respiration rate is the respiration rate per unit time.

As shown in FIG. 3, the $SpO_2$ meter 12 has a device body 12a, a probe section 12b, and a cable 12c connecting the device body 12a and the probe section 12b. The $SpO_2$ meter 12 has the probe section 12b fitted onto a finger of the patient 40, and measures the state of use by the patient 40 using the oxygen concentrator, as the $SpO_2$ value for blood flowing through the artery of the finger.

The $SpO_2$ meter 12 sends the measured usage data to the server 20 through the network N, using the communication terminal 13. The $SpO_2$ meter 12 communicates with the communication terminal 13 using short-range wireless communication, for example.

The communication terminal 13 sends the usage data received from the $SpO_2$ meter 12, to the server 20 through the network N, by wired or wireless communication.

The usage data measured by the $SpO_2$ meter 12 may include the $SpO_2$ value, pulse rate and acceleration, for example. The $SpO_2$ meter 12 measures the median or mean value for the $SpO_2$ as the recorded $SpO_2$ value. The pulse rate is the pulse rate per unit time. The acceleration is measured using an accelerometer in the $SpO_2$ meter 12, the server 20 determining the physical activity of the patient 40 based on the acceleration.

The server 20 receives usage data and operation data for the patient 40, and generates message information when either or both the usage data and operation data fail to satisfy the predetermined monitoring conditions. The server 20 also generates display information for the message information together with the usage data and operation data relating to the patient 40, and sends it to the monitoring terminals 30a, 30b through the network N.

The monitoring terminals 30a, 30b receive the display information for the message information together with the usage data and operation data relating to the patient 40, and display it. The monitoring terminal 30a is installed at the medical institution and is used by the physician in charge of the patient 40.

The physician in charge of the patient 40 can focus on the usage data or operation data for which message information was generated, which is displayed by the monitoring terminal 30a, to easily understand the state of use of the oxygen concentrator 10 and the condition of the patient 40. The physician may also compare the prescription written for the patient 40 with the usage data and operation data to confirm the state of use of the oxygen concentrator 10, the health condition of the patient 40 and compliance of the patient 40. The physician can thus confirm the therapeutic effect of the Home Oxygen Therapy for the patient 40, as support for devising future treatment policy for the patient 40.

The monitoring terminal 30b may also be used by medical personnel, for example, instead of a physician. Medical personnel other than a physician can also focus on the usage data or operation data for which message information was generated, to easily understand the condition of the patient 40. This will allow them to determine the necessary support or environment to be provided for the patient 40.

The physician in charge of the patient 40, using the monitoring terminal 30a, can authorize reception of the messages and the usage data and operation data for the patient 40 from the server 20, by the monitoring terminal 30b. This can prevent third parties from accessing personal information of the patient 40.

Figure 4:
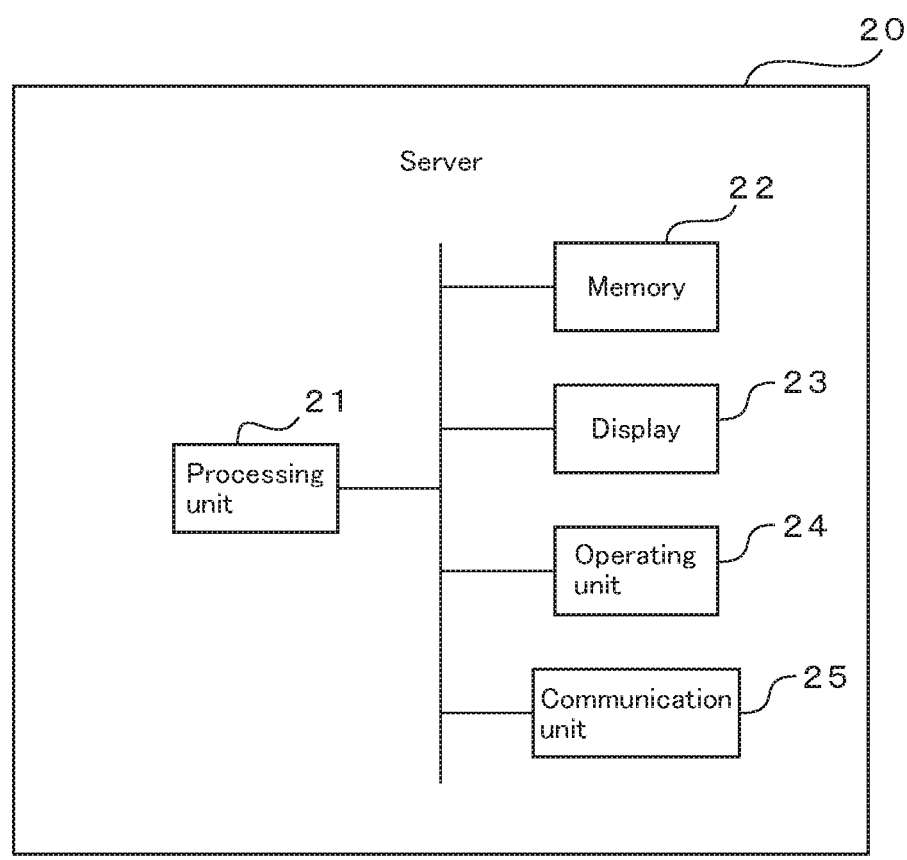
FIG. 4 is a diagram showing a server configuration.

FIG. 4 is a diagram showing a server configuration.

The server 20 has a processing unit 21, a memory 22, a display 23, an operating unit 24 and a communication unit 25.

The processing unit 21 has one or more processors, and a peripheral circuit. The processing unit 21 performs control of the hardware components of the server 20, and various processing, according to a predetermined computer program prestored in the memory 22, and uses the memory 22 for temporary storage of the data produced during processing.

The memory 22 may have a semiconductor memory such as a random access memory (RAM) or read-only memory (ROM), or a magnetic disk or flash memory. The memory 22 may also have a drive that is able to read a storage medium with non-temporary storage of a predetermined computer program. The memory 22 stores and associates identifying information for identification of the patient (patient ID), such as the patient name, birth date and gender, prescription information such as the oxygen flow rate, and future outpatient scheduling.

The display 23 is controlled by the processing unit 21 to display the various information. A liquid crystal display, for example, may be used as the display 23.

The operating unit 24 is operated by the user, allowing input operation. A keyboard or mouse, for example, may be used as the operating unit 24.

The communication unit 25 sends and receives information between the communication terminal 13 and the monitoring terminals 30a, 30b via the network N. The processing unit 21 carries out various processing based on the information received using the communication unit 25. The processing unit 21 sends results of the various processing using the communication unit 25. The communication unit 25 may have a communication circuit and communication line for sending and receiving.

Figure 5:
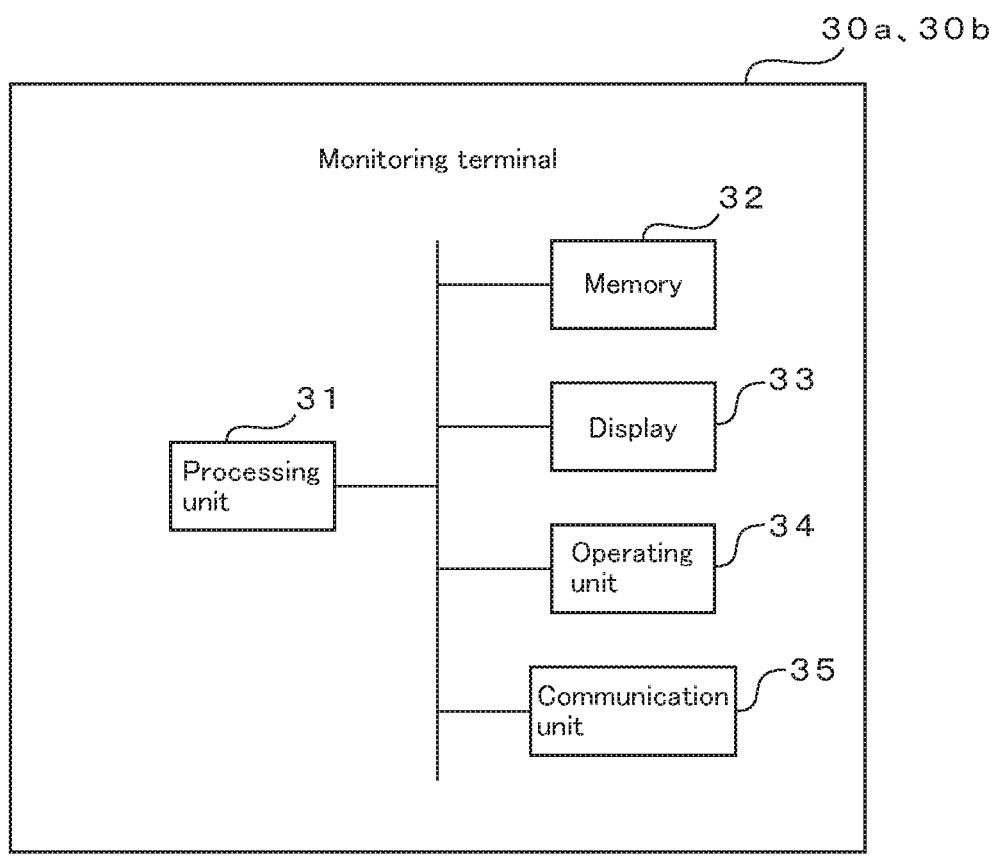
FIG. 5 is a diagram showing a monitoring terminal configuration.

FIG. 5 is a diagram showing monitoring terminals 30a, 30b.

The monitoring terminals 30a, 30b have a processing unit 31, a memory 32, a display 33, an operating unit 34 and a communication unit 35.

The processing unit 31 has one or more processors, and a peripheral circuit. The processing unit 31 performs control of the hardware components of the monitoring terminals 30a, 30b, and various processing, according to a predetermined computer program prestored in the memory 32, and uses the memory 32 for temporary storage of the data produced during processing.

The memory 32 may have a semiconductor memory such as a random access memory (RAM) or read-only memory (ROM), or a magnetic disk or flash memory. The memory 32 may also have a drive that is able to read a storage medium with non-temporary storage of a predetermined computer program.

The display 33 is controlled by the processing unit 31 to display the various information. A liquid crystal display, for example, may be used as the display 33.

The operating unit 34 is operated by the user, allowing input operation. A keyboard or mouse, for example, may be used as the operating unit 34.

The communication unit 35 sends and receives information with the server 20 via the network N. The processing unit 31 carries out various processing based on the information received using the communication unit 35. The processing unit 21 sends results of the various processing using the communication unit 35. The communication unit 35 may have a communication circuit and communication line for sending and receiving.

Figure 6A:
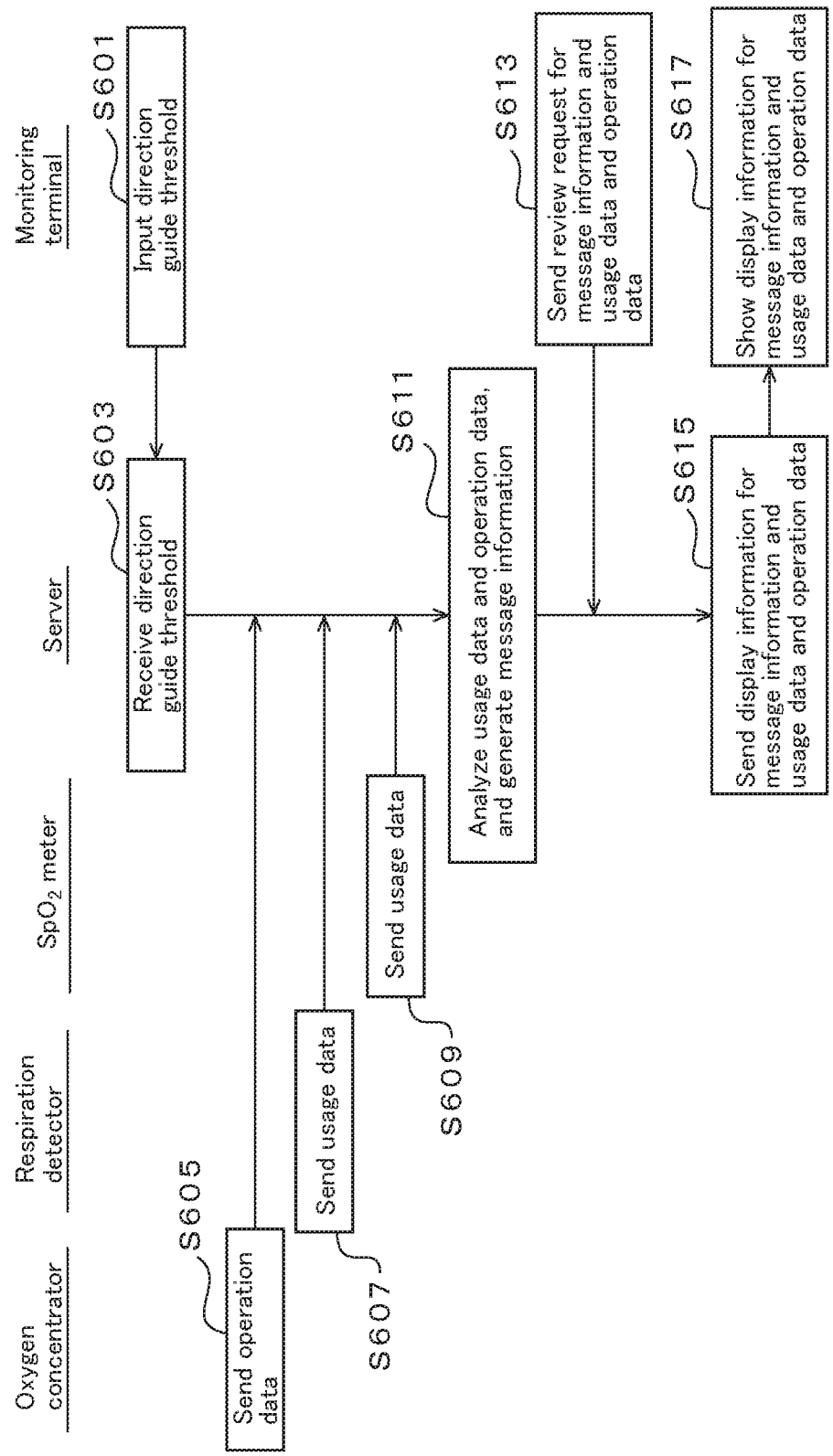
FIG. 6A is a sequence diagram (1) for a monitoring system.
Figure 6B:
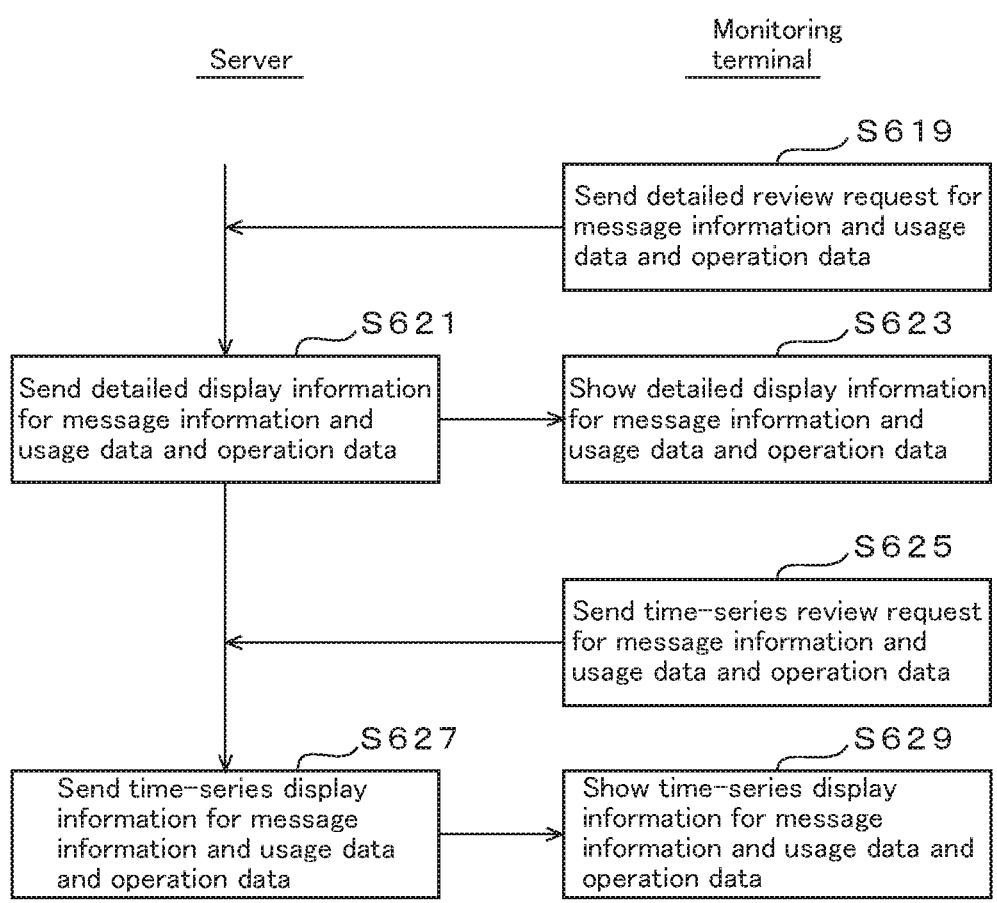
FIG. 6B is a sequence diagram (2) for a monitoring system.

Operation of the monitoring system 1 described above will now be described with reference to FIG. 6A and FIG. 6B.

First, in step S601, a physician at a medical institution operates the monitoring terminal 30a and inputs a direction guide threshold for a patient. The monitoring terminal 30a sends the direction guide threshold that the physician has input, together with the patient ID, for example, through the network N to the server 20. The direction guide threshold is an example of patient monitoring conditions relating to usage data and operation data. The direction guide threshold can be set for different individual patients. The direction guide threshold can also be set to be a common value for all patients overseen by the physician. The direction guide threshold can even be set to be a common value for all patients at the medical institution to which the physician belongs. The direction guide threshold may be set for all of the usage data and operation data, or set for only a portion of the usage data or operation data.

FIG. 7 is a screen 700 for the display 33 of the monitoring terminal 30a. The screen 700 displays a screen for input of direction guide thresholds. The screen 700 has an item column 701, a units column 702, an overall direction guide threshold column 703 spanning a predetermined period during which the oxygen concentrator 10 has been used, a direction guide threshold column 704 during resting periods during each day of use, a direction guide threshold column 705 for exertion periods during each day of use, a direction guide threshold column 706 for sleeping periods during each day of use, a direction guide threshold definition column 707, and a check column 708.

Each item in the item column 701 is an item of information that can be obtained or calculated by the server 20 based on the operation data or usage data.

The direction guide thresholds for each item are input with the units indicated in the units column 702.

The "inhalation time" in the item column 701 is the time during which the patient has inhaled oxygen using the oxygen concentrator 10. First, a direction guide threshold for the inhalation time is set as a lower limit for the daily use average, obtained by dividing the sum of the inhalation times for each day of use during the predetermined period during which the oxygen concentrator 10 has been used, by the number of days of use (direction guide threshold column 703). In the example shown in FIG. 7, 20 hours is set as the direction guide threshold for the inhalation time. A direction guide threshold for the inhalation time is also set as a lower limit for the daily use average for inhalation time when the oxygen concentrator 10 has been operated at the oxygen flow rate during resting periods, within the predetermined period during which the oxygen concentrator 10 is used (direction guide threshold column 704). A direction guide threshold for the inhalation time is similarly set as a lower limit for the daily use average for inhalation time when the oxygen concentrator 10 has been operated at the oxygen flow rate for exertion periods, within the predetermined period during which the oxygen concentrator 10 is used (direction guide threshold column 705). A direction guide threshold for the inhalation time is also set as a lower limit for the daily use average for inhalation time when the oxygen concentrator 10 has been operated at the oxygen flow rate for sleeping periods, within the predetermined period during which the oxygen concentrator 10 is used (direction guide threshold column 706). The server 20 generates message information when the inhalation time falls below any of the direction guide thresholds.

The non-prescription flow rate operating time in the item column 701 is the time during which the oxygen concentrator 10 has been operated at an oxygen flow rate outside of the flow rate prescribed by the physician. The physician's prescription determines the oxygen flow rate during resting periods, the oxygen flow rate during exertion periods and the oxygen flow rate during sleeping periods for each patient. The memory 22 of the server 20 stores the oxygen flow rate during resting periods, the oxygen flow rate during exertion periods and the oxygen flow rate during sleeping periods, in association with the patient ID. When the oxygen flow rate received as operation data does not match with the oxygen flow rate during resting periods, the oxygen flow rate during exertion periods or the oxygen flow rate during sleeping periods associated with the patient ID, the server 20 assesses that the oxygen concentrator 10 is being operated at a non-prescription flow rate. The direction guide threshold for the non-prescription flow rate operating time is set as the upper limit for the daily use average of operating time in which the oxygen concentrator 10 has been operated at a non-prescription flow rate, within the predetermined period during which the oxygen concentrator 10 is used. In the example shown in FIG. 7, 30 minutes is set as the direction guide threshold for the non-prescription flow rate operating time. The server 20 generates message information when the non-prescription flow rate operating time is above the direction guide threshold for the non-prescription flow rate operating time.

The operation time in item column 701 is the time during which the oxygen concentrator 10 has been operated. A direction guide threshold for the operation time is first set as a lower limit for the daily use average for operation time when the oxygen concentrator 10 has been operated, within the predetermined period during which the oxygen concentrator 10 is used (direction guide threshold column 703). A direction guide threshold for the operation time is also set as a lower limit for the daily use average for operation time when the oxygen concentrator 10 has been operated at the oxygen flow rate during resting periods, within the predetermined period during which the oxygen concentrator 10 is used (direction guide threshold column 704).

A direction guide threshold for the operation time is also set as a lower limit for the daily use average for operation time when the oxygen concentrator 10 has been operated at the oxygen flow rate during oxygen flow rate during exertion periods, within the predetermined period during which the oxygen concentrator 10 is used (direction guide threshold column 705). A direction guide threshold for the operation time is similarly set as a lower limit for the daily use average for operation time when the oxygen concentrator 10 has been operated at the oxygen flow rate during sleeping periods, within the predetermined period during which the oxygen concentrator 10 is used (direction guide threshold column 706). The server 20 generates message information when the operation time falls below any of the direction guide thresholds for the operation time.

A direction guide threshold for the cannula dislocation time in item column 701 is first set as an upper limit for the daily use average for operation time when the oxygen concentrator 10 has been operated in a state where cannula dislocation has been detected, within the predetermined period during which the oxygen concentrator 10 is used (direction guide threshold column 703). In the example shown in FIG. 7, 2 hours is set as the direction guide threshold for the cannula dislocation time. A direction guide threshold for the cannula dislocation time is also set as an upper limit for the daily use average for operation time when the oxygen concentrator 10 has been operated at the oxygen flow rate during resting periods in a state where cannula dislocation has been detected, within the predetermined period during which the oxygen concentrator 10 is used (direction guide threshold column 704). In the example shown in FIG. 7, 30 minutes is set as the direction guide threshold for the cannula dislocation time. A direction guide threshold for the cannula dislocation time is also set as an upper limit for the daily use average for operation time when the oxygen concentrator 10 has been operated at the oxygen flow rate during exertion periods in a state where cannula dislocation has been detected, within the predetermined period during which the oxygen concentrator 10 is used (direction guide threshold column 705). In the example shown in FIG. 7, 30 minutes is set as the direction guide threshold for the cannula dislocation time. A direction guide threshold for the cannula dislocation time is also set as an upper limit for the daily use average for operation time when the oxygen concentrator 10 has been operated at the oxygen flow rate during sleeping periods in a state where cannula dislocation has been detected, within the predetermined period during which the oxygen concentrator 10 is used (direction guide threshold column 706). In the example shown in FIG. 7, 1 hour is set as the direction guide threshold for the cannula dislocation time. The server 20 generates message information when the cannula dislocation time is above any of the direction guide thresholds for the cannula dislocation time.

The cannula bend alarm count in the item column 701 is the number of cannula bend alarms that have been generated during the predetermined period during which the oxygen concentrator 10 is used. A direction guide threshold for the cannula bend alarm count is first set as the upper limit for the number of cannula bend alarms that have been generated during the predetermined period during which the oxygen concentrator 10 is used (direction guide threshold column 703). A direction guide threshold for the cannula bend alarm count is also set as an upper limit for the number of cannula bend alarms generated when the oxygen concentrator 10 has been operated at the oxygen flow rate during resting periods, within the predetermined period during which the oxygen concentrator 10 is used (direction guide threshold column 704). A direction guide threshold for the cannula bend alarm count is also set as an upper limit for the number of cannula bend alarms generated when the oxygen concentrator 10 has been operated at the oxygen flow rate during exertion periods, within the predetermined period during which the oxygen concentrator 10 is used (direction guide threshold column 705). A direction guide threshold for the cannula bend alarm count is similarly set as an upper limit for the number of cannula bend alarms generated when the oxygen concentrator 10 has been operated at the oxygen flow rate during sleeping periods, within the predetermined period during which the oxygen concentrator 10 is used (direction guide threshold column 706). The server 20 generates message information when the cannula bend alarm count is above any of the direction guide thresholds for the cannula bend alarm count.

The $SpO_2$ value in the item column 701 can be set as a median value or an average value. The direction guide threshold for the $SpO_2$ value is first set as the lower limit for the daily use average of the $SpO_2$ value, within the predetermined period during which the oxygen concentrator 10 is used (direction guide threshold column 703). In the example shown in FIG. 7, the direction guide threshold for the $SpO_2$ value is set to 85%. The direction guide threshold for the $SpO_2$ value is also set as a lower limit for the daily use average for the $SpO_2$ value measured when the oxygen concentrator 10 has been operated at the oxygen flow rate during resting periods, within the predetermined period during which the oxygen concentrator 10 is used (direction guide threshold column 704). In the example shown in FIG. 7, the direction guide threshold for the $SpO_2$ value is set to 85%. The direction guide threshold for the $SpO_2$ value is also set as a lower limit for the daily use average for the $SpO_2$ value measured when the oxygen concentrator 10 has been operated at the oxygen flow rate during exertion periods, within the predetermined period during which the oxygen concentrator 10 is used (direction guide threshold column 705). In the example shown in FIG. 7, the direction guide threshold for the SpO$_2$ value is set to 85%. The direction guide threshold for the SpO$_2$ value is also set as a lower limit for the daily use average for the SpO$_2$ value measured when the oxygen concentrator 10 has been operated at the oxygen flow rate during sleeping periods, within the predetermined period during which the oxygen concentrator 10 is used (direction guide threshold column 706). In the example shown in FIG. 7, the direction guide threshold for the SpO$_2$ value is set to 85%. The server 20 generates message information when the SpO$_2$ value falls below any of the direction guide thresholds for the SpO$_2$ value.

The pulse rate in the item column 701 can be set as a median value or an average value. A direction guide threshold for the pulse rate is first set as a lower limit for the daily use average for the pulse rate within the predetermined period during which the oxygen concentrator 10 is used (direction guide threshold column 703). In the example shown in FIG. 7, 80 bpm is set as the direction guide threshold for the pulse rate. The direction guide threshold for the SpO$_2$ value is also set as a lower limit for the daily use average for the SpO$_2$ value measured when the oxygen concentrator 10 has been operated at the oxygen flow rate during resting periods, within the predetermined period during which the oxygen concentrator 10 is used (direction guide threshold column 704). In the example shown in FIG. 7, 80 bpm is set as the direction guide threshold for the pulse rate. The direction guide threshold for the SpO$_2$ value is also set as a lower limit for the daily use average for the SpO$_2$ value measured when the oxygen concentrator 10 has been operated at the oxygen flow rate during exertion periods, within the predetermined period during which the oxygen concentrator 10 is used (direction guide threshold column 705). In the example shown in FIG. 7, 80 bpm is set as the direction guide threshold for the pulse rate. The direction guide threshold for the SpO$_2$ value is also set as a lower limit for the daily use average for the pulse rate measured when the oxygen concentrator 10 has been operated at the oxygen flow rate during sleeping periods, within the predetermined period during which the oxygen concentrator 10 is used (direction guide threshold column 706). In the example shown in FIG. 7, 80 bpm is set as the direction guide threshold for the pulse rate. The server 20 generates message information when the pulse rate falls below any of the direction guide thresholds for the pulse rate.

The check column 708 indicates whether or not a direction guide threshold has been set for each item in the item column 708. An item that is checked in the check column 708 has a direction guide threshold set, and one that is not checked does not have any direction guide threshold set.

In the example shown in FIG. 7, direction guide thresholds are set for the inhalation time, the non-prescription flow rate operating time, the cannula dislocation time, the SpO$_2$ value and the pulse rate. No direction guide threshold is set for the operation time and cannula bend alarm count.

Next, in step S603, the server 20 stores the received direction guide thresholds for each item in a memory 22 associated with the patient ID.

In the following step S605, the oxygen concentrator 10 begins sending the patient ID and operation data to the server 20 through the network N, using the communication terminal 13. For example, the oxygen concentrator 10 sends operation data to the server 20 at predetermined intervals, or after a change in the state of operation has taken place. The server 20 stores the received operation data in association with the patient ID. When operation data is received from the oxygen concentrator 10 even once in a single day, the server 20 assesses that the patient has used the oxygen concentrator 10, and adds it as a day of use. The server 20 also discriminates between resting period operation, exertion period operation and sleeping period operation, based on the set value for the oxygen flow rate received from the oxygen concentrator 10. The server 20 also calculates the operation time of the oxygen concentrator 10 based on the date and time of the operation data received from the oxygen concentrator 10. The server 20 further calculates the non-prescription flow rate operating time based on the set value for the oxygen flow rate received from the oxygen concentrator 10, and the reception date and time. The server 20 still further calculates the flow switching count, which is the number of times that setting of the oxygen flow rate has been changed, based on the set values for the oxygen flow rate received from the oxygen concentrator 10. The server 20 determines the cannula bend alarm count during a predetermined period, based on cannula bend alarm notifications received from the oxygen concentrator 10.

In the following step S607, the respiration detector 11 begins sending the patient ID and the measured usage data to the server 20 through the network N, using the communication terminal 13. For example, the respiration detector 11 sends usage data to the server 20 at predetermined intervals, or when a change in usage data has occurred. The server 20 stores the received usage data in association with the patient ID. The server 20 calculates the oxygen inhalation time based on the date and time when the respiration detection notification has been received as usage data. The server 20 also calculates the cannula dislocation time, based on the date and time when the cannula dislocation notification has been received, as usage data. The cannula dislocation time is presumed to be the time of the state in which the patient 40 has not inhaled oxygen.

In the following step S609, the SpO$_2$ meter 12 begins sending the patient ID and the measured usage data to the server 20 through the network N, using the communication terminal 13. For example, the SpO$_2$ meter 12 sends usage data to the server 20 at predetermined intervals, or when a change in usage data has occurred. The server 20 stores the received usage data in association with the patient ID. The server 20 calculates the amount of movement of the patient based on the acceleration, as received usage data, and estimates the physical activity of the patient based on the amount of movement.

This order of processing of steps S605 to S609 is just an example, and a different order may be used.

In the following step S611, the server 20 analyzes the usage data and operation data for each patient by comparing it with the direction guide thresholds stored in the memory 22, and generates message information when the usage data fails to satisfy the conditions stipulated by the direction guide thresholds and/or when the operation data fails to satisfy the conditions stipulated by the direction guide thresholds.

The message information may also include, for example, a notification that usage data and/or operation data has fallen outside the conditions stipulated by the direction guide threshold, or a proposal to monitor the condition of the patient, or a proposal to re-evaluate the manner in which the oxygen concentrator 10 is to be used by the patient.

Generation of the message information may also include generating display information in which usage data or operation data that does not satisfy the conditions stipulated by the direction guide thresholds is displayed in a visibly enhanced manner. Generation of the message information may also include selecting one or more items of message information from among previously prepared message information items, based on the usage data or operation data that does not satisfy the conditions stipulated by the direction guide thresholds.

The server 20 may also generate message information based on the usage data and operation data. For example, when the inhalation time has fallen below the direction guide threshold and the non-prescription flow rate operating time is above the direction guide threshold, the server 20 may generate message information reading: "Please confirm patient compliance, or re-evaluate prescription if necessary". When the non-prescription flow rate operating time has fallen below the direction guide threshold and the non-prescription flow rate operating time is above the direction guide threshold, it is possible that the patient is not carrying out oxygen inhalation based on the prescription, and therefore presumably compliance should be ensured, or it may be necessary to re-evaluate the prescription. When the $SpO_2$ value has fallen below the direction guide threshold and the pulse rate has fallen below the direction guide threshold, the server 20 may generate message information reading: "Confirm condition of patient immediately". When the $SpO_2$ value has fallen below the direction guide threshold and the pulse rate has fallen below the direction guide threshold, it is possible that the patient may be in a dangerous state of health, and therefore it may be necessary for the physician or medical personnel to immediately confirm the condition of the patient.

The following are other specific examples of message information to be generated by the server 20. For example, when the non-prescription flow rate operating time is above the direction guide threshold, the server 20 may generate message information reading: "Excessive time operating at non-prescription flow rate". When the pulse rate is above the direction guide threshold, the server 20 may generate message information reading: "Pulse rate exceeds target value". When the non-prescription flow rate operating time is above the direction guide threshold and the $SpO_2$ value has fallen below the direction guide threshold, the server 20 may generate message information reading: "$SpO_2$ value has fallen. Please take note of non-prescription flow rate operating time". When the $SpO_2$ value has fallen below the direction guide threshold, the respiration rate is above the direction guide threshold, and the operation time has fallen below the direction guide threshold, the server 20 may generate message information reading: "$SpO_2$ value is low and respiration rate has increased. Please confirm patient compliance, or re-evaluate prescription if necessary". The generated message information is not limited to the particular instances described above.

Next, in step S613, the physician at the medical institution uses the monitoring terminal 30a to send a review request to review the message information together with the usage data and operation data for the patient in their charge, along with the desired review period and the patient ID, to the server 20 through the network N.

In the following step S615, the server 20 generates display information that, based on the received review request, displays message information together with the usage data and operation data for the patient under the charge of the physician, and sends it to the monitoring terminal 30a through the network N.

In the following step S617, the monitoring terminal 30a displays the message information, together with the usage data and operation data of the patient under the charge of the physician, on the display 33, based on the received display information.

FIG. 8 is a diagram showing the screen 800 of a display 33 that displays the overall situation for the state of operation and state of use for a patient under the charge of a physician.

The screen 800 shows information of different items over a predetermined period during which an oxygen concentrator 10 has been used, for each of the patients under the charge of the physician.

The screen 800 has a patient ID column 801, a patient name column 802, a patient gender column 803, a used day count column 804 for the oxygen concentrator 10, an operating time column 805 for the oxygen concentrator 10, a cannula dislocation time column 806, a cannula bend alarm count column 807, a non-prescription flow rate operating time column 808, an $SpO_2$ value column 809, a patient next scheduled outpatient date column 810 and a check column 811.

The patient ID and patient birth date are displayed in the patient ID column 801. The server 20 accesses information stored in the memory 22, based on the patient ID in the review request, reads out the patient ID and patient birth date that are to be displayed in the patient ID column 801, and generates the display information in the patient ID column 801. The server 20 generates display information for the patient name column 802 and patient gender column 803 in a similar manner.

In the used day count column 804, the number of days of use of the oxygen concentrator 10 is displayed for each patient. The server 20 accesses information stored in the memory 22, based on the patient ID, and generates display information for the number of days of use over the predetermined period during which the oxygen concentrator 10 has been used.

In the operating time column 805, the daily use average for the operation time over the predetermined period during which the oxygen concentrator 10 has been used is displayed, for each patient. The server 20 accesses information stored in the memory 22, based on the patient ID, and generates display information for the daily use average for the operation time of the oxygen concentrator 10.

In the cannula dislocation time column 806, the daily use average for cannula dislocation time over the predetermined period during which the oxygen concentrator 10 has been used is displayed, for each patient. The server 20 accesses information stored in the memory 22, based on the patient ID, and generates display information for the daily use average for cannula dislocation time.

In the cannula bend alarm count column 807, the cannula bend alarm count over the predetermined period during which the oxygen concentrator 10 has been used is displayed, for each patient. The server 20 accesses information stored in the memory 22, based on the patient ID, and generates display information for the cannula bend alarm count.

In the non-prescription flow rate operating time column 808, the daily use average for the non-prescription flow rate operating time over the predetermined period during which the oxygen concentrator 10 has been used is displayed, for each patient. The server 20 accesses information stored in the memory 22, based on the patient ID, and generates display information for the daily use average for non-prescription flow rate operating time.

In the $SpO_2$ value column 809, the daily use average for the $SpO_2$ value over the predetermined period during which the oxygen concentrator 10 has been used is displayed, for each patient. The server 20 accesses information stored in the memory 22, based on the patient ID, and generates display information for the daily use average for the SpO₂ value.

In the next scheduled outpatient date column 810, the next scheduled outpatient date is displayed for each patient. The server 20 accesses information stored in the memory 22, based on the patient ID, and generates display information for the next scheduled outpatient date.

The generated message information is displayed on the screen 800, for each item of each patient. In the example on this screen 800, the message information is generated as display information to be displayed with the item information visibly enhanced.

This will allow the physician to quickly observe the items for which message information was generated, for the predetermined period during which the oxygen concentrator 10 has been used, for each patient.

The screen 800 shown in FIG. 8 is merely an example, and the invention is not limited to the screen 800 example shown in FIG. 8.

In the following step S619, when it is desired to confirm the details of the operation data and usage data relating to use of the oxygen concentrator 10 for one patient, the physician checks the check column 811 of that patient using the monitoring terminal 30a. The monitoring terminal 30a sends the checked patient ID and a detailed review request, requesting detailed display information for the message information, usage data and operation data, to the server 20.

Next, in step S621, upon receiving the patient ID and the detailed review request, the server 20 generates detailed display information for the message information, usage data and operation data relating to the patient identified by the patient ID, and sends it to the monitoring terminal 30a.

In the following step S623, the monitoring terminal 30a displays the detailed display information for the message information, usage data and operation data of the patient on the display 33, based on the received detailed display information.

FIG. 9 is a diagram showing a display screen 900 of a display 33 that displays the detailed situation for the state of operation and state of use for a patient.

The screen 900 has a message column 901, a usage overview table 902, a usage details table 903 and an SpO₂ pulse rate table 904.

Generated message information is displayed in the message column 901. In the example shown in FIG. 9, the message information displayed in the message column 901 has been generated for items that fail to satisfy the conditions stipulated by the overall direction guide threshold column 703 for the predetermined period during which the oxygen concentrator 10 has been used, shown in the screen 700, as a number of messages that can be displayed in an easily visible manner in the message column 901. The number of message information items displayed in the message column 901 may be set as appropriate for the dimensions of the message column 901, for example. For example, all of the generated message information items may be displayed in the message column 901.

Specifically, in the example shown in FIG. 9, message information items generated for the inhalation time, the non-prescription flow rate operating time, the operation time, the cannula dislocation time and the cannula bend alarm count are displayed in the message column 901.

The usage overview table 902 has an item column 902a, a first period column 902b, a second period column 902c and a third period column 902d.

The number of days of use of the oxygen concentrator 10, the inhalation time, the flow switching count and the non-prescription flow rate operating time for a predetermined period are displayed in the item column 902a. The information items other than the number of days of use displayed in the usage overview table 902 are daily use averages for the predetermined period during which the oxygen concentrator 10 has been used.

Each information item for the period from March 1 to March 30 is displayed in the first period column 902b. Message information for the inhalation time and non-prescription flow rate operating time is generated, and the information items are displayed in a visibly enhanced manner in the first period column 902.

Detailed information for each item during the same period as the first period column 902b is displayed in the usage details table 903 and SpO₂ pulse rate table 904.

Information for each item during the period of January 30 to February 28 is displayed in the second period column 902c. Information for each item during the period of December 31 to January 29 is displayed in the third period column 902d.

The usage details table 903 has an item column 903a, an overall information column 903b in which the daily use average or cumulative value for each item during the predetermined period during which the oxygen concentrator 10 has been used is displayed, a resting period information column 903c in which the daily use average or cumulative value for each item during resting periods is displayed, an exertion period information column 903d in which the daily use average or cumulative value for each item during exertion periods is displayed, an "other information column" 903e in which the daily use average or cumulative value for each item during other periods of the day is displayed, a sleeping period information column 903f in which the daily use average or cumulative value for each item during sleeping periods is displayed, and an "other information column" 903g in which the daily use average or cumulative value for each item during other periods of the night is displayed.

The operation time, the cannula dislocation time and the cannula bend alarm count are displayed in the item column 903a.

In the "other information column" 903e for other periods of the day, the daily use average or cumulative value for each item during periods other than resting periods and exertion periods is displayed. In the "other information column" 903g for other periods of the night, the daily use average or cumulative value for each item with an oxygen flow rate in periods other than sleeping periods is displayed. Here, "night" is defined as the period from 10:00 pm to 5:00 am, and "day" is defined as the period from 5:00 am to 10:00 pm.

In the example shown in FIG. 9, message information is generated for the operation time, the cannula dislocation time and the cannula bend alarm count, and the item information is displayed in a visibly enhanced manner.

The SpO₂ pulse rate table 904 has an item column 904a, an overall information column 904b in which the daily use average for each item in the predetermined period during which the oxygen concentrator 10 has been used is displayed, a resting period information column 904c in which the daily use average for each item during resting periods is displayed, an exertion period information column 904d in which the daily use average 4 for each item during exertion periods is displayed, an "other information column" 904e in which the daily use average 4 for each item during other periods of the day is displayed, a sleeping period information column 904f in which the daily use average 4 for each item during sleeping periods is displayed, and an "other information column" 904g in which the daily use average 4 for each item during other periods of the night is displayed.

Information for the SpO$_2$ value and pulse rate is displayed in the item column 904a.

In the "other information column" 904e for other periods of the day, the daily use average 4 for each item during periods other than resting periods and exertion periods is displayed. In the "other information column" 903g for other periods of the night, the daily use average for each item with an oxygen flow rate in periods other than sleeping periods is displayed.

This will allow the physician to quickly observe detailed information for items with generated message information for the predetermined period during which the oxygen concentrator 10 has been used, for a single patient.

By displaying message information at the top end of the screen 900 of the display 33 while displaying usage data and operation data at the lower end of the screen 900 of the display 33, as shown in FIG. 9, the physician is able to confirm, on the same screen, both the message information and the usage data and/or operation data for which message information has been generated, thus facilitating overall observation of the condition of the patient.

The screen 900 shown in FIG. 9 is merely an example, and the invention is not limited to the screen 900 example shown in FIG. 9.

Next, in step S625, if it is desired to confirm the time series information for the message information, usage data and operation data relating to use of the oxygen concentrator 10 by a single patient, the physician sends a time series review request, requesting review of the time series information, together with the patient ID.

Next, in step S627, upon receiving the patient ID and the time series review request, the server 20 generates display information for the time series information for the message information, usage data and operation data relating to the patient identified by the patient ID, and sends it to the monitoring terminal 30a.

In the following step S629, the monitoring terminal 30a displays the display information for the time series information for the message information, usage data and operation data of the patient identified by the patient ID, on the display 33, based on the received display information for the time series information.

Figure 10:
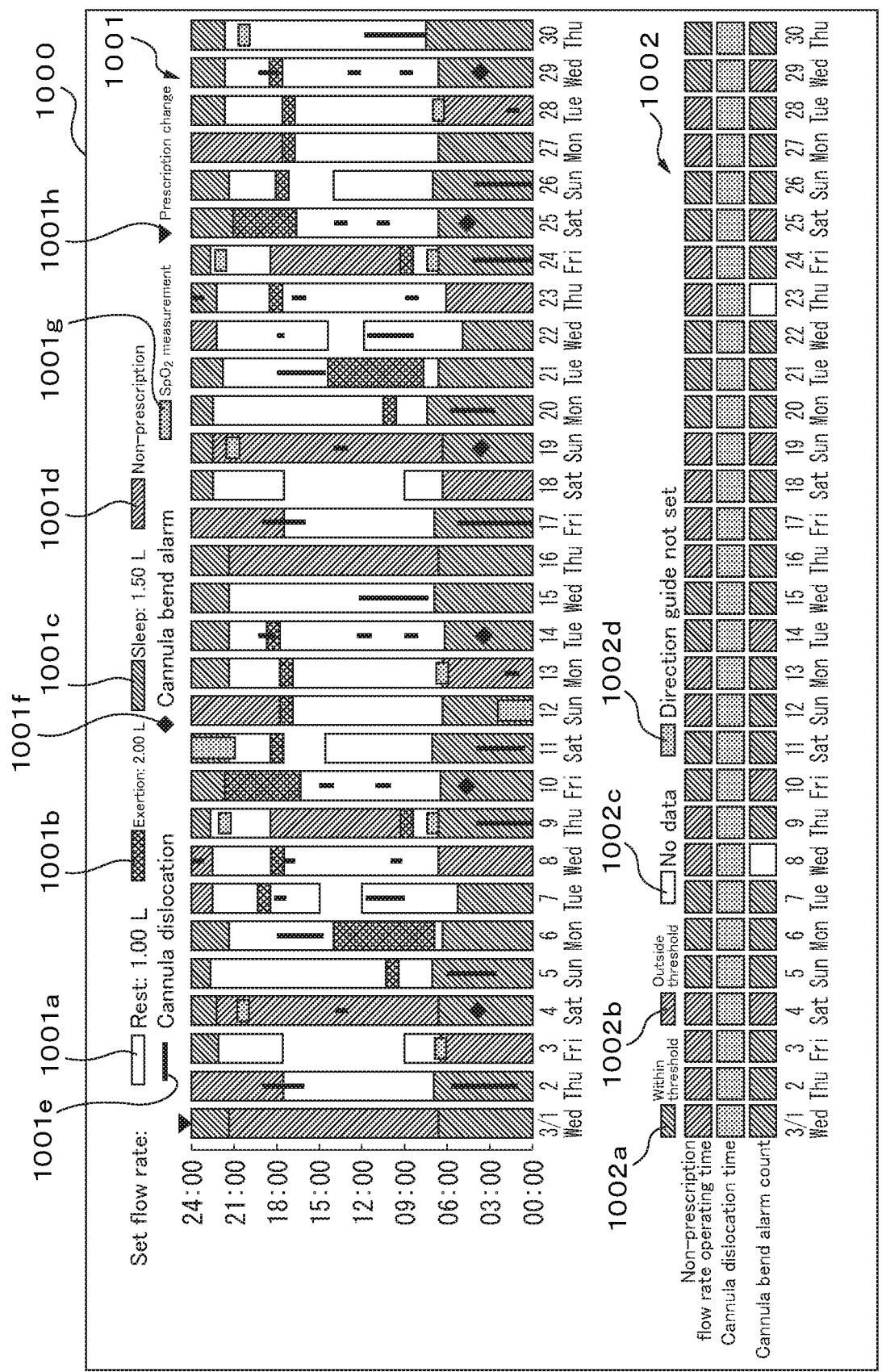
FIG. 10 is a diagram showing a display screen that displays the state of operation and state of use for a patient, in a time series.

FIG. 10 is a diagram showing a screen 1000 of a display 33 that displays the state of operation and state of use for a patient, in a time series.

The screen 1000 has a first time series information region 1001 and a second time series information region 1002.

In the first time series information region 1001, a time series is displayed horizontally for the dates for which usage data and operation data have been acquired, with the set values for the oxygen flow rate being displayed vertically in a time series for each date of acquisition. The set values for the oxygen flow rate are classified by resting period 1001a, exertion period 1001b, sleeping period 1001c and non-prescription 1001d. In the first time series information region 1001, usage data and operation data are displayed vertically in a time series for each date of acquisition. In the example shown in FIG. 10, cannula dislocation occurrence 1001e, cannula bend alarm occurrence 1001f and generation of SpO$_2$ value message information 1001g are displayed in a time series. In the first time series information region 1001, a date 1001h in which the prescription for the patient was changed is displayed.

In the second time series information region 1002, the dates of acquisition for which usage data and operation data have been acquired are displayed in a time series, showing whether or not message information has been generated for a predetermined item for each date of acquisition. In the example shown in FIG. 10, the non-prescription flow rate operating time, cannula dislocation time and cannula bend alarm count are displayed as items. Dates of acquisition without generation of message information are displayed as being outside of the direction guide threshold 1002b, and dates of acquisition with generation of message information are displayed as being within the direction guide threshold 1002a. Incidentally, since no direction guide threshold value has been set for the cannula dislocation time, it is displayed as having an unset direction guide threshold 1002d. Dates for which usage data and operation data items have not been acquired are indicated as having no data 1002c.

This allows the physician to easily observe the time series information for items with generated message information in the predetermined period during which the oxygen concentrator 10 has been used, for a single patient, thus aiding in understanding time-related changes in the condition of the patient.

The screen 1000 shown in FIG. 10 is merely an example, and the invention is not limited to the screen 1000 example shown in FIG. 10.

The monitoring system of the embodiment described above can monitor usage data indicating the state of use by a patient using the oxygen concentrator and operation data indicating the state of operation of the oxygen concentrator, and can notify a monitoring person, such as a physician, by generation of a message when predetermined monitoring conditions fail to be satisfied.

In the embodiment described above, the monitoring terminal 30a is used by the physician in charge of the patient. The monitoring terminal 30b may also be used by medical personnel instead of the physician, under the supervision of the physician. Medical personnel other than the physician can also operate the monitoring terminal 30b to observe the usage data and operation data shown in FIG. 8 to FIG. 11. This will allow the physician and medical personnel other than the physician to share patient information, thus aiding them in efficiently establishing future treatment policy for the patient and providing the necessary support and environment for the patient.

The server, monitoring system, terminal, monitoring device and method of the embodiment described above according to the invention may implement appropriate modifications such as are within the scope of the gist thereof.

The operation data for the oxygen concentrator and the usage data for the measuring apparatus are merely examples, and the invention is not limited to those oxygen concentrator operation data and measuring apparatus usage data.

Furthermore, the monitoring system in the embodiment described above comprises two monitoring terminals, but the number of monitoring terminals is not limited to two. It is sufficient for the monitoring system to comprise at least one monitoring terminal, or it may comprise three or more monitoring terminals.

A plurality of monitoring terminals may also be disposed at different medical institutions to allow their use by different physicians. This will allow the condition of the patient to be examined by more than one physician with different specialties.

In the embodiment described above, the monitoring terminal displays message information, usage data and operation data on a display, but the server, functioning as a monitoring device, may instead output the message information, usage data and operation data using an output device such as a server display.

The embodiment described above also has the server generate message information when either or both the usage data and operation data fail to satisfy the monitoring conditions, but the monitoring terminal or server, as a monitoring device, may instead input the usage data and operation data using an input device such as a communication unit, the processing unit of the monitoring terminal or server generating message information when either or both the usage data and operation data fail to satisfy the monitoring conditions, and using an output device such as a monitoring terminal or server display to output the message information, usage data and operation data.

REFERENCE SIGNS LIST

1 Monitoring system
10 Oxygen concentrator
11 Respiration detector
12 SpO$_2$ meter
12a Device body
12b Probe section
12c Cable
13 Communication terminal
14 Cannula
20 Server
21 Processing unit
22 Memory
23 Display (output device)
24 Operating unit
25 Communication unit (input device, output device)
30a, 30b Monitoring terminal
31 Processing unit
32 Memory
33 Display (output device)
34 Operating unit
35 Communication unit (input device, output device)
40 Patient
700 Screen
701 Item column
702 Units column
703 Overall direction guide threshold column
704 Resting period direction guide threshold column
705 Exertion period direction guide threshold column
706 Sleeping period direction guide threshold column
707 Definition column
708 Check column
800 Screen
801 Patient ID column
802 Patient name column
803 Gender column
804 Used day count column
805 Operating time column
806 Cannula dislocation time column
807 Cannula bend alarm count column
808 Non-prescription flow rate operating time column
809 SpO$_2$ column
810 Next scheduled outpatient date column
811 Check column
900 Screen
901 Message column
902 Usage state overview table
902a Item column
902b First period column
902c Second period column
902d Third period column
903 Usage state details table
903a Item column
903b Overall information column
903c Resting period information column
903d Exertion period information column
903e Other daytime information column
903f Sleeping period information column
903g Other nighttime information column
904 SpO$_2$ pulse rate table
904a Item column
904b Overall information column
904c Resting period information column
904d Exertion period information column
904e Other daytime information column
904f Sleeping period information column
904g Other nighttime information column
1000 Screen
1001 First time series information region
1002 Second time series information region

The invention claimed is:

1. A server for monitoring of the state of use of an oxygen concentrator that concentrates oxygen in air and supplies the oxygen to a user, the server comprising:
a communication device; and
a processor configured to use the communication device to receive operation data indicating the state of operation of the oxygen concentrator and usage data for the state of use by the user using the oxygen concentrator, measured by a measuring apparatus, while also configured to generate message information when either or both the usage data and the operation data fail to satisfy monitoring conditions, and send the message information to a medical terminal which requires a review request together with the usage data and the operation data in response to the review request from the medical terminal, using the communication device, wherein
the monitoring conditions include a direction guide threshold relating to the operation data or the usage data, spanning a predetermined period during which the oxygen concentrator has been used, and
the message information includes user's compliance information relating to the operation data or the usage data not satisfying the monitoring conditions specified by the direction guide threshold.

2. The server according to claim 1, wherein the processor is configured to generate the message information based on the usage data and the operation data.

3. The server according to claim 1, wherein the message information includes:
a notification that the usage data has fallen outside the monitoring conditions, or a proposal to monitor a condition of the user, or a proposal to re-evaluate the manner in which the oxygen concentrator is to be used by the user.

4. The server according to claim 1, wherein the processor is configured to use the communication device to send display information for display of the message information on the first side of a screen of a display, and display of the usage data and the operation data on the second side of the screen of the display, to a terminal comprising the display.

5. The server according to claim 1, wherein the processor is configured to use the communication device to send display information for display of a time series for the message information and the usage data and the operation data on the display, to a terminal comprising the display.

6. The server according to claim 5, wherein the processor is configured to use the communication device to send the display information for display of the usage data and the operation data to the terminal in a time series, for each of a plurality of dates of acquisition for which the usage data and the operation data have been acquired.

7. The server according to claim 1, wherein the operation data includes an oxygen flow rate setting value or a cannula bend alarm notification.

8. The server according to claim 1, wherein the usage data includes a respiration detection notification notifying that respiration of the user has been detected, a cannula dislocation notification, a respiration rate, an arterial blood oxygen saturated concentration or a pulse rate.

9. A monitoring system for monitoring of the state of use of an oxygen concentrator that concentrates oxygen in air and supplies the oxygen to a user, comprising:
    an oxygen concentrator that sends operation data indicating the state of operation;
    a measuring apparatus that measures and sends usage data indicating the state of use by the user using the oxygen concentrator;
    a server that receives the usage data and the operation data, and when either or both the usage data and the operation data fail to satisfy monitoring conditions, generates message information and sends the message information together with the usage data and the operation data in response to a review request; and
    a medical terminal that has a display, sends the review request to the server and receives the message information together with the usage data and the operation data from the server, displaying the message information together with the usage data and the operation data on the display, wherein
    the monitoring conditions include a direction guide threshold relating to the operation data or the usage data, spanning a predetermined period during which the oxygen concentrator has been used, and
    the message information includes user's compliance information relating to the operation data or the usage data not satisfying the monitoring conditions specified by the direction guide threshold.

10. The monitoring system according to claim 9, which comprises a plurality of medical terminals,
    wherein one of the plurality of medical terminals is able to authorize reception of the message information, the usage data and the operation data from the server by one of the other medical terminals among the plurality of medical terminals.

11. A terminal for monitoring of the state of use of an oxygen concentrator that concentrates oxygen in air and supplies the oxygen to a user, comprising:
    a communication device;
    a display; and
    a processor configured to use the communication device to receive from a server in response to a review request message information generated by the server that has received operation data indicating the state of operation of the oxygen concentrator and usage data for the state of use by the user using the oxygen concentrator, measured by a measuring apparatus, when either or both the usage data and the operation data fail to satisfy the monitoring conditions, and also the usage data and the operation data, and display the message information together with the usage data and the operation data on the display, wherein
    the monitoring conditions include a direction guide threshold relating to the operation data or the usage data, spanning a predetermined period during which the oxygen concentrator has been used, and
    the message information includes user's compliance information relating to the operation data or the usage data not satisfying the monitoring conditions specified by the direction guide threshold.

12. A monitoring device for monitoring of the state of use of an oxygen concentrator that concentrates oxygen in air and supplies the oxygen to a user, comprising:
    an input device;
    an output device; and
    a processor configured to carry out to input operation data indicating the state of operation of the oxygen concentrator and usage data for the state of use by the user using the oxygen concentrator using the input device, and when either or both the usage data and the operation data fail to satisfy monitoring conditions, carry out to generate message information and output the message information together with the usage data and the operation data using the output device in response to a review request from a medical terminal, wherein
    the monitoring conditions include a direction guide threshold relating to the operation data or the usage data, spanning a predetermined period during which the oxygen concentrator has been used, and
    the message information includes user's compliance information relating to the operation data or the usage data not satisfying the monitoring conditions specified by the direction guide threshold.

13. The monitoring device according to claim 12, further comprising a display as the output device,
    wherein the processor is configured to carry out to display the message information together with the usage data and the operation data on the display.

14. A method for monitoring the state of use of an oxygen concentrator that concentrates oxygen in air and supplies the oxygen to a user, wherein the method comprises:
    obtaining, by a server, operation data indicating the state of operation of the oxygen concentrator and usage data for the state of use by the user using the oxygen concentrator;
    generating, by the server, message information when either or both the usage data and the operation data fail to satisfy monitoring conditions and sending the message to a terminal; and
    displaying, by the terminal, the message information together with the usage data and the operation data, on a display in response to a review request from a medical terminal, wherein
    the monitoring conditions include a direction guide threshold relating to the operation data or the usage data, spanning a predetermined period during which the oxygen concentrator has been used, and
    the message information includes user's compliance information relating to the operation data or the usage data not satisfying the monitoring conditions specified by the direction guide threshold.

* * * * *